(12) United States Patent
Neuwirth

(10) Patent No.: US 10,912,946 B2
(45) Date of Patent: Feb. 9, 2021

(54) DEVICE FOR GENERATING ALTERNATING MAGNETIC FIELDS FOR INDUCING EDDY CURRENTS IN AN ORGANISM

(71) Applicant: CLEANHEARING INC., Lewes, DE (US)

(72) Inventor: Gerald Neuwirth, Spittal/Drau (AT)

(73) Assignee: CLEANHEARING INC., Lewes, DE (US)

( * ) Notice: Subject to any disclaimer, the term of this patent is extended or adjusted under 35 U.S.C. 154(b) by 219 days.

(21) Appl. No.: 16/064,576

(22) PCT Filed: Dec. 7, 2016

(86) PCT No.: PCT/AT2016/000098
§ 371 (c)(1),
(2) Date: Jun. 21, 2018

(87) PCT Pub. No.: WO2017/106884
PCT Pub. Date: Jun. 29, 2017

(65) Prior Publication Data
US 2019/0009101 A1    Jan. 10, 2019

(30) Foreign Application Priority Data

Dec. 23, 2015 (AT) .................................. A 820/2015
Sep. 20, 2016 (AT) .................................. A 430/2016

(51) Int. Cl.
*A61N 2/00* (2006.01)
*A61M 21/02* (2006.01)
(Continued)

(52) U.S. Cl.
CPC .............. *A61N 2/004* (2013.01); *A61B 5/128* (2013.01); *A61M 21/00* (2013.01); *A61N 2/002* (2013.01);
(Continued)

(58) Field of Classification Search
CPC ............. H04R 2209/041; H04R 25/75; A61M 2205/502; A61M 2021/0066;
(Continued)

(56) References Cited

U.S. PATENT DOCUMENTS

| 6,162,166 A * | 12/2000 | Neuwirth ................. A61N 2/02 600/14 |
| 2008/0150669 A1* | 6/2008 | Kawai ................. H01F 27/2847 336/222 |
| 2012/0203130 A1 | 8/2012 | Bernhard |

FOREIGN PATENT DOCUMENTS

| DE | 103 10 084 A1 | 9/2004 |
| EP | 0 537 385 A1 | 4/1993 |

(Continued)

OTHER PUBLICATIONS

International Search Report, dated May 2, 2017 (3 pages).
Japanese Office Action (English translation only) dated Sep. 1, 2020.

*Primary Examiner* — Christine H Matthews
*Assistant Examiner* — Joshua Daryl D Lannu
(74) *Attorney, Agent, or Firm* — Jacobson Holman, PLLC

(57) ABSTRACT

A device for generating alternating magnetic fields for inducing eddy currents in an organism in order to treat tinnitus comprising a head part, a current source, a controller, and one or more coils. At least one coil has at least two layers with a different winding, whereby alternating magnetic fields can be generated more effectively for inducing eddy currents in an organism in order to treat tinnitus.

16 Claims, 2 Drawing Sheets

(51) Int. Cl.
*A61N 2/02* (2006.01)
*H04R 25/00* (2006.01)
*A61M 21/00* (2006.01)
*A61B 5/12* (2006.01)

(52) U.S. Cl.
CPC ............... *A61N 2/02* (2013.01); *A61M 21/02* (2013.01); *A61M 2021/0027* (2013.01); *A61M 2021/0033* (2013.01); *A61M 2021/0055* (2013.01); *A61M 2021/0066* (2013.01); *A61M 2205/3553* (2013.01); *A61M 2205/3569* (2013.01); *A61M 2205/3584* (2013.01); *A61M 2205/3592* (2013.01); *A61M 2205/368* (2013.01); *A61M 2205/502* (2013.01); *A61M 2205/505* (2013.01); *A61M 2205/52* (2013.01); *A61M 2205/8206* (2013.01); *A61N 2/006* (2013.01); *A61N 2/008* (2013.01); *H04R 25/75* (2013.01); *H04R 2209/041* (2013.01)

(58) Field of Classification Search
CPC .... A61M 2205/368; A61M 2205/3584; A61M 2021/0033; A61M 2205/3569; A61M 21/02; A61M 2205/3592; A61M 2021/0055; A61M 21/00; A61M 2021/0027; A61M 2205/8206; A61M 2205/505; A61M 2205/3553; A61M 2205/52; A61N 2/02; A61N 2/006; A61N 2/002; A61N 2/008; A61N 2/004; A61B 5/128

See application file for complete search history.

(56) References Cited

FOREIGN PATENT DOCUMENTS

| | | |
|---|---|---|
| JP | 2001/029379 | 2/2001 |
| JP | 2001501856 | 2/2001 |
| JP | 2006254524 | 9/2006 |
| KR | 10-2010-0078190 A | 7/2010 |
| KR | 10-2014-0108030 A | 9/2014 |
| WO | 99/04854 A1 | 2/1999 |
| WO | 2014/020960 | 2/2004 |
| WO | 2011/009807 A1 | 1/2011 |
| WO | 2012/168543 A1 | 12/2012 |

* cited by examiner

DEVICE FOR GENERATING ALTERNATING MAGNETIC FIELDS FOR INDUCING EDDY CURRENTS IN AN ORGANISM

FIELD OF THE INVENTION

The present invention relates to a device for generating alternating magnetic fields. The present invention, in particular, relates to a device for generating alternating magnetic fields for inducing eddy currents in an organism for treating tinnitus in particular, comprising
  a head part,
  a current source,
  a controller,
  one or more coils.

The present invention refers to a device for generating alternating magnetic fields for inducing eddy currents in an organism and the use of such a device. The device for generating and emitting alternating magnetic fields is designed to have an adjustable low frequency with pulses, sharp edges and harmonics.

PRIOR ART

Various devices for generating and emitting alternating electromagnetic fields for treating and examining organisms are known, wherein it is generally to be anticipated that the penetration depth of such alternating electromagnetic fields is a function of the frequency.

WO 2011/009807 describes a tinnitus therapy device comprised of a combination between an applicator for low-frequency electromagnetic fields (therapy) and an electroencephalography (EEG) as source for the evaluation of the therapeutic effects (diagnosis). The patent application WO 2011/009807 does not give any hints as to the manner in which the iron-core coils of the applicators are wound.

WO 1999/04854 describes a device for generating alternating magnetic fields for inducing eddy currents in an organism. Again, the patent application WO 1999/04854 does not contain any hints as to the manner how the iron-core coils of the applicators are wound.

Further similar devices for treating tinnitus of the initially defined kind can, for instance, be taken from DE 103 10 084 A1 or EP 0 537 385 A1, wherein, again, no details relating to the winding of the coils or solenoids used in such devices are disclosed.

SUMMARY OF THE INVENTION

It is an object of the present invention to propose a novel and improved device that enables to more effectively generate alternating magnetic fields for inducing eddy currents in an organism for treating tinnitus in particular.

To solve this object, a device of the initially defined kind is substantially characterized in that the at least one coil comprises at least two layers with different windings.

The present invention aims to provide a device for generating alternating magnetic fields for inducing eddy currents in an organism, by which eddy currents can be selectively and safely generated in an organism in a structurally simple manner so as to enable, by the induced stimulation of the autonomic nervous system, a selective control of possible charge shifts in the cell membranes, and/or the removal or reduction of existing blockages. Since alternating magnetic fields of an adjustable low frequency are emitted by the device according to the invention, the simple adaptation to different sensitivities of different organisms has become possible. In this context, it was found that the sensitivity is highest at a frequency that corresponds to the EEC alpha rhythm of the person to be treated. The low field strengths selected according to the invention, moreover, ensure that the desired effects in regard to the induction of eddy currents in an organism can be achieved by problem-free and absolutely safely handling. In doing so, pulses in wave-form with pulsating, sharp edges including harmonics are generated and emitted. These induced pulses delivered to the organism will optimally excite and support the organism's own pulses if the frequency of the externally applied alternating magnetic fields is synchronous with the intrinsic pulses. The sought stimulation of the autonomic nervous system will thus be aided.

An essential characteristic feature of the device according to the invention resides in that the at least one coil comprises at least two layers with different windings. As in contrast to conventional coils, on which the wire is wound in regularly superimposed layers, the at least one coil of the device according to the invention is configured with at least two layers having different windings. Due to this special winding method, the alternating magnetic field is given special properties in connection with the induction of eddy currents in an organism. The different coils may be wound according to the same pattern so as to enable the automation or reproducibility of the production of the coils. The coils are, for instance, designed to produce a magnetic field of up to 2 mT.

The configuration provided according to the invention, of the at least one coil with at least two layers having different windings enables the production or provision of coils that are substantially better able to generate sharp pulses with harmonic content. Such coils for the production of sharp pulses with harmonic content definitely show better effects in the treatment of, in particular, tinnitus than normally wound coils.

According to a particularly preferred embodiment, it is provided according to the invention that the at least one coil comprises at least one layer with an orthocyclic winding and at least one layer with a helical winding. Such a coil configuration comprising at least one layer with an orthocyclic winding and at least one layer with a helical winding enables the reliable achievement of the above-mentioned sharp harmonic pulses in a coil operated with extremely low frequencies.

In order to enhance the intended effects of specially designed pulses, it is proposed according to a further preferred embodiment of the invention that the at least one coil comprises a plurality of adjacent layers each with orthocyclic and helical windings.

To allow for particularly reliable and precise positioning of the coils for generating alternating magnetic fields for inducing eddy currents in an organism at the locations or positions chosen for the treatment of, in particular, tinnitus, it is proposed according to a further preferred embodiment of the invention that the at least one coil is disposed in or on a headphone, in particular in or on an ear cup of a headphone.

In order to obtain the eddy currents to be induced at the desired locations, in particular for treating tinnitus, it is, moreover, proposed according to a further preferred embodiment that two coils are each assigned to each ear on different height levels. The coils to be assigned to each ear are attached or positioned in the regions of the cortex and of the mastoid, wherein the cortex coils are, for instance, located in the upper region of the ear cup of a headphone, while the coils for the mastoid are attached to the lower side of the ear cup of the head part or headphone, in particular in a slightly oblique manner. The special arrangement of the coils to be assigned to each ear on different height levels as proposed by the invention ensures that the force field produced by the electromagnetic fields will also reach cells in the interior of the body in order to achieve the desired effect.

In this context, it is it is proposed according to a further preferred embodiment that the coils assigned to each ear are operated in the push-pull mode. Such a push-pull operation of the coils assigned to each ear causes the produced alternating electromagnetic fields to act on electric charges, thus setting static charges in the auditory center in motion, in particular in the rhythm of their own vibrations. Due to the push-pull operation of the coils, weak reverberation signals overlaid on the pulsating alternating electromagnetic field are generated, which are of therapeutic relevance, since they are able to, in particular, stimulate the exchange of information between the cells.

A particularly simple configuration of the invention, which is easy to produce in terms of construction, is preferably devised such that the device comprises an astable multivibrator with a transistor, and at least one bipolar iron-core coil for emitting the alternating fields. The generation and emission of the alternating magnetic fields can be accomplished relatively simply and cost-effectively with known elements. The device according to the invention can, in particular, be used for treating ear noises, sleep disorder, headache, migraine, cervical and thoracic syndromes, nervousness and circulatory disorder. It has been demonstrated that favorably acting portions of the alternating magnetic fields with adjustable, low frequencies are selected such that the frequency is below 20 Hz, in particular between 3 and 15 Hz. In general, a classification into two essential treatment-specific domains was found, a frequency range between 3 and 6 Hz generally having a calming and spasmolytic effect. By contrast, a frequency range of between 8 and 15 Hz mainly has stimulating, analgesic and stabilizing effects. It may further be anticipated that frequencies below 8 Hz basically have vasodilating effects, while frequencies above 12 Hz will generally lead to vasoconstrictions, wherein the above-indicated high frequency range should only be applied where lower frequencies are ineffective.

To further improve the adaptation of the frequency to be adjusted to the desired effect, it is proposed according to a further preferred embodiment that, in particular digital, wobbling of the frequency by ±50%, preferably ±25%, preferably ±10%, is provided.

For a structurally simple construction and, in particular, for the fabrication of devices that can be operated independently of a grid, it is, moreover, proposed according to a further preferred embodiment that a low-voltage direct voltage source, in particular a 9 volt direct voltage source, is provided as voltage supply. It is thus also possible in a simple manner to make mobile and portable gadgets independent of a mains supply, by providing a battery as direct voltage supply, which is of particular advantage when applied in the treatment of tinnitus. Rechargeable accumulators can also be easily integrated as power sources.

As already indicated above, the device according to the invention can be used for treating a plurality of application fields, wherein, in particular for the treatment of ear noises or tinnitus as pointed out above, the device is received in a headphone with a bipolar iron-core coil being included in each loudspeaker of the headphone. Optionally, a configuration comprising just one bipolar iron-core coil is, however, also conceivable, if, for instance, ear noises occur in only one ear. A device according to the invention can be readily realized in such a headphone, optionally with an appropriate small-structured accessory device, such that, overall, a construction easy to apply and use will be achieved.

In a variant embodiment the device according to the invention comprises an input device and a display device. As already indicated above, an essential characteristic feature of the device according to the invention resides in the availability of adjustable, low frequencies for treating various indications and for obtaining the best possible correspondence between the alternating magnetic fields and the intrinsic pulses of the person to be treated. In this context, it is proposed that the device comprises a plurality of switches or selection means for adjusting a desired frequency, duration of the therapy, start/stop of the therapy. It has thus become possible in a simple manner to achieve both an adaptation to desired frequency ranges and as precise a correspondence with the frequency of the intrinsic pulses of the person to be treated.

In a variant embodiment, the mastoid and cortex coils are electrically controlled individually and disposed such that the respective signals are shifted in time by any desired value. A signal shift by half a period between the mastoid coil and the cortex coil on one head side will, for instance, encourage special healing effects.

To further facilitate the handling and monitoring of the device according to the invention, it is, moreover, preferably provided that the device comprises at least one display, in particular an LCD display or a retina display. To further automate the use of the device according to the invention, it is proposed that the device comprises a timer as in correspondence with a further preferred embodiment of the invention.

In a variant embodiment, the device according to the invention comprises two or more loudspeakers to combine the magnetic field therapy with a sound therapy. Tinnitus-specific sound sequences, calming music pieces, maskers or noisers are emitted via the loudspeakers. The loudspeakers are, for instance, connected to a music player via an audio port or via a contactless data interface such as Bluetooth. The control of the playing of music is performed via a Bluetooth-capable device such as a smartphone. The volume and the title can be directly shown on the display device and triggered by the input device. Alternatively, a suitable selection can be made by using an additional, small remote controller.

In a variant embodiment, the device according to the invention comprises areas that can be heated and are in contact with, or close to, the skin. Such heated areas will additionally promote the blood flow. Tensions and spasms in the ear region will thus be relieved. Heating is, for instance, effected by radiators operating in the infrared range.

In a variant embodiment, the device according to the invention comprises a data interface, e.g. a wired interface such as an audio port for connecting a music player or an external controller for the operation or maintenance of the device according to the invention, or e.g. a wireless interface such as Bluetooth for connecting a smartphone. In a variant embodiment, the device according to the invention comprises an interface by which the device can be connected to Fitbit bracelets and smart watches, enabling data exchanges. In a variant embodiment, the device according to the invention comprises an interface by which the device can be connected to IoT (Internet of Things), i.e. the network. To this end, an RFID transponder is integrated in the circuit.

In a variant embodiment, the device according to the invention comprises a memory module, for instance a memory card, e.g. an SD card, for storing relaxation music and tinnitus-healing music, which is emitted by the loudspeakers. Measurement data or therapy protocols can also be deposited on the memory card for subsequent evaluation.

In a variant embodiment, some functions of the device according to the invention are outsourced to a base part. In such a configuration, the head part, for instance, comprises the headband, the ear cups, the applicators, the loudspeakers, while the base part comprises the remaining components such as the current source, the controller, the display device, the input device etc. This variant embodiment will be of particular advantage, if certain components are heavy, space-requiring and only difficult to integrate in the head part. The connection between the head part and the base part is, for instance, realized via a cable or via a contactless interface such as Bluetooth. Certain functions may likewise be integrated in a smartphone in the sense of an app. In this case, a device-specific app is downloaded from an app store and installed on the smartphone. The input and display means of the smartphone can be used as input and display means for the device according to the invention. Such a variant embodiment provides savings for the patient. The communication between the smartphone and the device according to the invention takes place via a contactless interface, e.g. Bluetooth, and enables a data exchange in both directions, namely from the smartphone to the device according to the invention for control purposes, and from the device according to the invention to the smartphone for diagnostic purposes.

BRIEF DESCRIPTION OF THE DRAWINGS

In the following, the invention will be explained in more detail by way of exemplary embodiments schematically illustrated in the accompanying drawing. Therein.

DETAILED DESCRIPTION OF PREFERRED EMBODIMENTS

The invention will be explained in more detail below with reference to the Figures.

Figure 1:
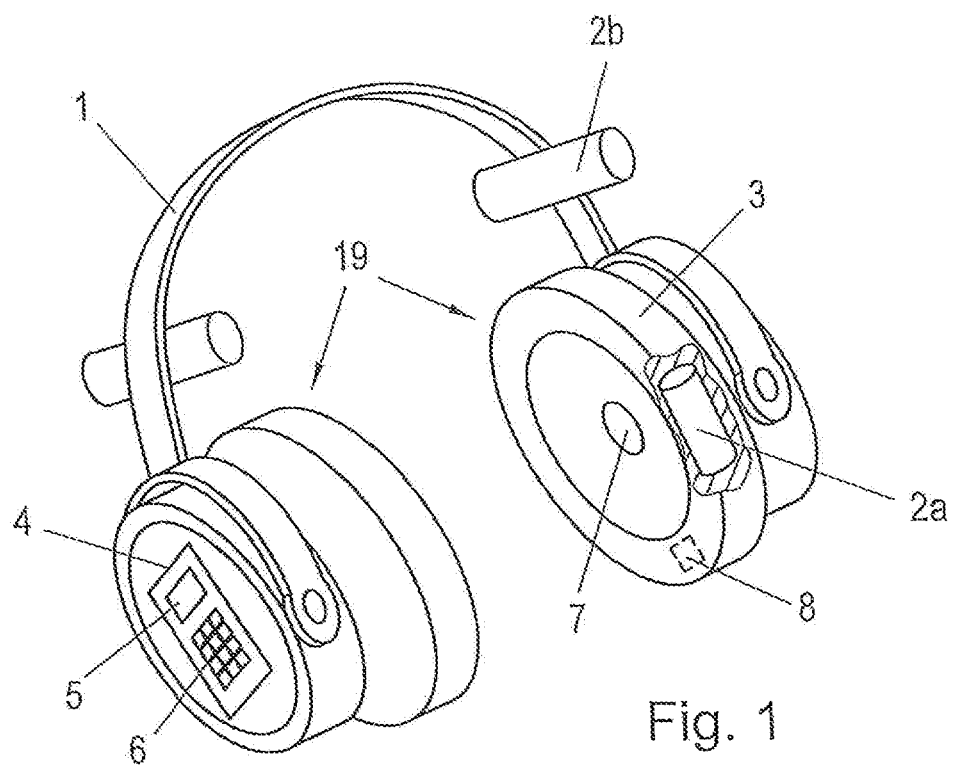
FIG. 1 is a schematic illustration of a first embodiment of a device according to the invention.

The device according to FIG. 1, for instance, comprises a headphone 1, also referred to as head part, including a spring-mounted headband and two ear cups covering the ears. For the head part, high-quality material is used to ensure maximum comfort during therapy. All materials have been tested for skin tolerance. An applicator 2, e.g. an iron-core coil 2*a*, is each provided in the ear cups. They are provided for treating the mastoid bones and are directly cast into the rear region of an ear cup. The mastoid bone is a curved bone; it is located immediately behind the ear. Other applicators, e.g. iron-core coils 2*b* for the cortex, are also directly cast into the headband 1 so that they will not move during use. The cortex (or also called cerebral cortex) is the outermost layer of the cerebrum and rich in nerve cells. In a variant embodiment, the iron-core coils are cast into tabs attached to the headband 1 and which are moved until a specific position of the cortex is reached. A current source 3, for instance a battery or a rechargeable accumulator, is disposed on the headband 1 or in the ear cups. A controller 4 and a signal amplifier (not illustrated) for amplifying the applicator signals are housed in the ear cups or in the headband. This electronics will, at the same time, monitor the actual functioning of the applicators. This is done by measuring the current flow to the head part.

FIG. 1, moreover, indicates a display 5, an input device 6, a loudspeaker 7 and heating pads or heated areas 8 in or on each ear cup 19 of the headphone 1.

Figure 2:
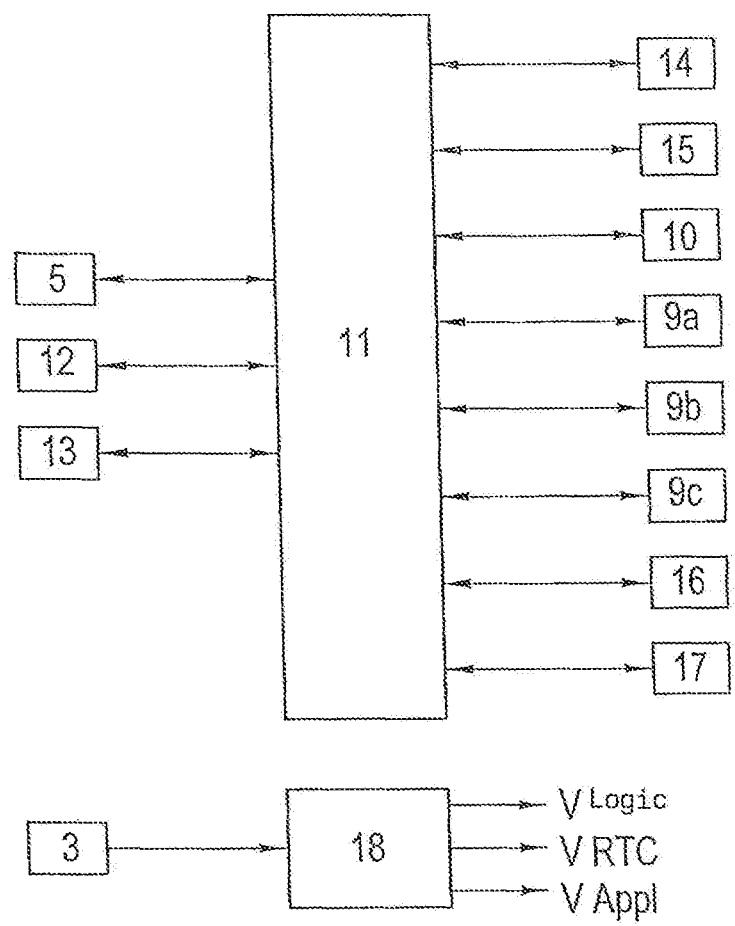
FIG. 2 is a schematic circuit arrangement of the embodiment according to FIG. 1.

The device comprises a controller, which will be described in more detail below with reference to FIG. 2. The electronics of the controller should be based on the most modern SMT technology, which would result in substantially reduced manufacturing costs. In a variant embodiment, the electronics of the controller, including the display and the input device 6, is supplied in the head part of the device according to the invention, the entire device according to the invention thus enabling a completely wireless therapy contributing to stress reduction.

The controller 4 of the device according to the invention comprises the following components:

Controller 11: for instance from the ATMEGA 16-P type by Atmel with a 10 Kbyte internal program memory, 2K RAM and 28 byte EEPROM. The program memory is designed as a flash program memory, and hence erasable and programmable up to 10,000 times.

EEPROM 12: The following data are deposited in the EEPROM: up to 10 curve shapes of 256 bytes each (2,560 bytes), a running time meter (8 bytes), patient data (256 bytes), time programs (256 bytes). Hence results a total of 3,080 bytes. In order to be prepared for the future, a serial EEPROM of 64 Kbits is used (e.g. AT24C64 by Atmel).

RTC 13: The RTC (real time clock) enables the recording and retrieval of the exact times and date of every single treatment in the storage module 10.

Reset 14: The supervisory circuit supervises the supply voltage and will emit a defined RESET signal for the processor unit if the defined limit value is fallen short of. This happens both in the power-up case and in case of a brown-out. Furthermore, the module switches the supply for the RTC module in the off-state of the device.

Clock 15: Clock frequency of 8 MHz for the clock supply of the controller 11. Due to the required accuracy of the clock frequency, a ceramic resonator is used.

Display 5: A retina HD display is preferred. Its operation is done by a separate app. The overall control 4, of the individual components is likewise provided by separate apps. It is, however, also possible to include foreign tinnitus apps (masker, trainer or noiser) in the operation.

USB port: This connection serves to charge the integrated accumulators. Furthermore, the USB port may be used for program updates and data exchange with a PC.

D/A converter 16: The D/A converter generates the output signal to the applicator according to a curve shape deposited in the EEPROM. The resolution of the amplitude and of the frequency is to be 256 (=time-discrete and amplitude-discrete output).

PWM output: In this case, a PWM signal is emitted by the controller 11. Amplitude defined via DA converter.

Output amplifier 17: This amplifies to the maximum amplitude the applicator signal emitted by the DA converter and, at the same time, monitors the actual functioning of the applicators (head part). This is effected by measuring the current flow (signal APPL OK) to the head part, which is measured, and assessed accordingly, by the analog/digital converter of the controller 11. Based on this measurement, an assessment of the applicator function is possible. The applicators selected by the app are addressed to with the same signals.

Bluetooth: The control 4, 24 comprises a Bluetooth module. It is thus possible to output music or the tinnitus app to the tinnitus device via the head part by means of a smartphone or a Bluetooth-capable player. The control 4, 24 may be effected via the smartphone.

Audio port: A non-capable smartphone or player can also be connected via the audio port, and the tinnitus trainer, masker or noiser can be emitted via the head part.

SD memory card: By using an SD memory card, it is possible to load special relaxing or tinnitus music into the device and emit the same via the head part.

Audio: To this end, the audio module (MS6331G) is used. The volume and the title can be directly selected from the display 5, 25 (display device) or smartphone.

Voltage processing 18: The device is supplied by an internal accumulator. The following voltages are processed: VLogic: Supply voltage for the logic part and Bluetooth module 3.3 V. VAppl: Applicator voltage for the output amplifier. VRTC: Backup voltage for RTC 13 and real time. Furthermore, the voltage processor 18 also monitors the accumulator voltage (LOWBAT) and feeds it to the AD converter of the controller 11. The latter measures the voltage to enable early indication of necessary charging. The development is realized considering power-saving components.

Infrared heat: Infrared heating pads 8 are incorporated in the ear pads (ear cup). They will additionally promote blood circulation. Tensions and spasms in the ear region will thus be relieved.

Applicator coils: The coils for the mastoid bone are directly cast into the rear part of the ear cup. The coils for the cortex are also directly cast into the headband 1, 21 so as to prevent them from moving during use. A high-quality head part is used in order to ensure maximum comfort during therapy. All materials have been tested for skin intolerances.

The application comprises the following functions:

Applicator signal: Ten curve shapes can be stored, simultaneously, superimposed or combined. The selection is effected via the display.

Maximum frequency of the applicator: 200 Hz.

An important component of the frequency comprises additional wobbling.

The frequencies are selected in different programs.

Running time meter from 0-9999 (saving and read-out in ¹/₁₀ hours) and read-out on display.

State monitoring accumulator (LOWBAT) and read-out on display.

State monitoring applicator (APPLOK) and read-out on display.

Connected Bluetooth display (DL link) and read-out on display.

SD memory card—titles individually selectable and controllable. Read-out on display.

Volume control for audio output higher/lower (<</>>) and read-out on display.

Applicators for cortex and/or mastoid can be individually turned on and off and read-out on display.

Menu guidance and apps on display.

Time monitoring and automatic shutdown of the display (background illumination) and/or the controller 11.

BUSY indication on display to indicate the "READY" state on the device.

Storage of data in EEPROM, e.g. running time meter, number of started treatments.

USB port for making program changes and charging the accumulator.

The processing of the patient data can be done via an upload. The data can then be processed using a PC and separate software.

In a variant embodiment, the coils are comprised of an iron core. The dimension of the iron core comprises a length of 30 mm to 60 mm, in particular 50 mm to 60 mm, and a diameter of 6 mm. The coil has 600 to 650 windings of a copper wire with a diameter of 0.2 mm.

Figure 3:
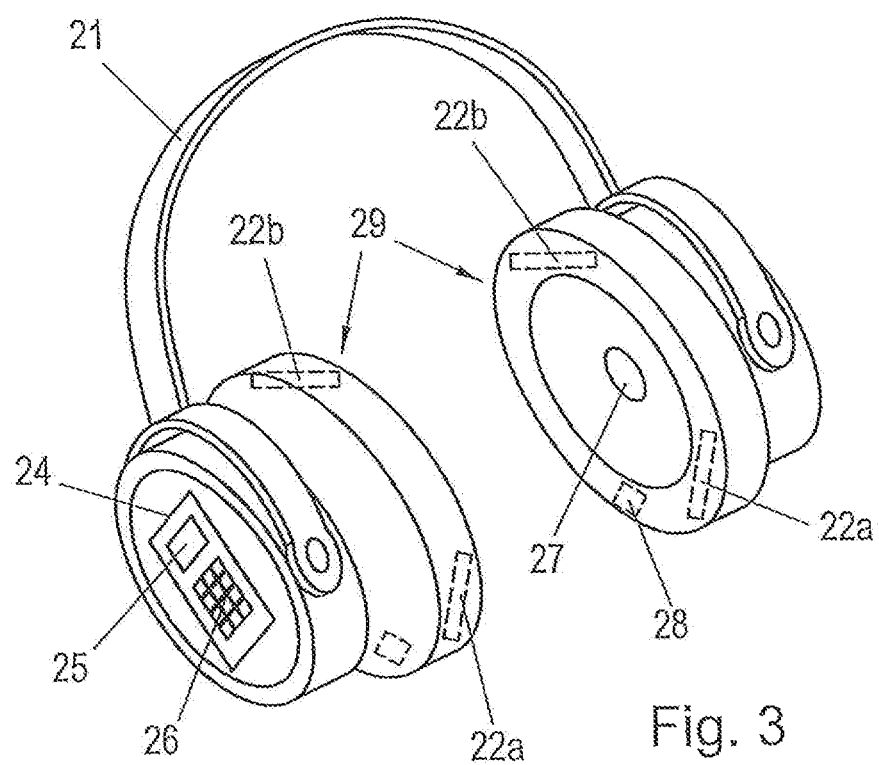
FIG. 3 illustrates a modified embodiment of a device according to the invention in a representation similar to that of FIG. 1.

In the embodiment according to FIG. 3, a plurality of coils is again integrated in a headphone 21 or, in particular, the ear cups 29 of the headphone, whereby it is apparent that in the embodiment illustrated in FIG. 3 both the coils 22a for the mastoid and the coils 22b for the cortex are integrated in the ear cups 29 of the headphone, each on a different height level.

Similarly as in the embodiment according to FIG. 1, additional elements such as a controller 24, a display 25, an input device 26, a loudspeaker 27 and areas to be heated or heating pads 28 are likewise each integrated, and schematically indicated, in the ear cups 29 of the headphone.

Figure 4:
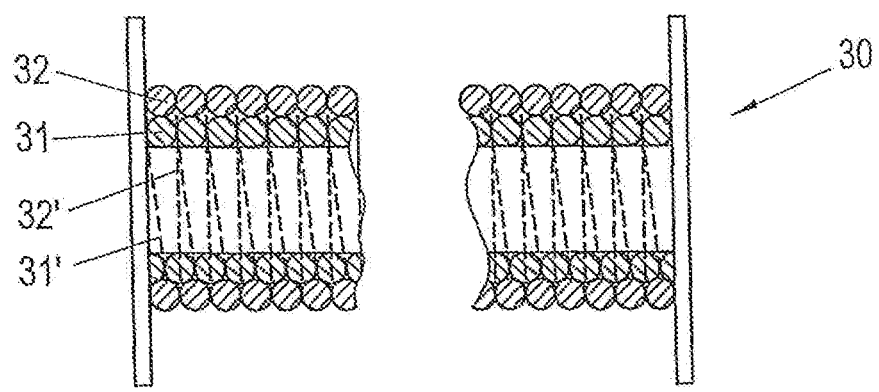
FIG. 4 depicts, on an enlarged scale, a partially schematic illustration of a coil with layers having different windings.

FIG. 4 schematically depicts, in an enlarged illustration no to scale, a partially sectioned coil 30, from which it is apparent that a first winding layer denoted by 31 is helically wound as shown by the course 31' of the wires of this layer 31, which is indicated in broken lines.

Consecutively thereto, a layer 32 is indicated, whose wires are orthocyclically wound as shown by the schematically indicated course 32, and which extends substantially normally to the coil axis opposite the oblique or inclined arrangement of the helical winding 31 or 31', respectively.

By providing layers 31, 32 with different windings, it is, in particular, possible to obtain fields with sharp harmonic pulses as opposed to coils having uniform or constant windings, such cases being, in particular, obtainable in a push-pull operation of the coils 2a and 2b, and 22a and 22b, respectively, assigned to each ear.

Depending on the field strength to be achieved, the coil 30, which is only schematically indicated in FIG. 4 and may be used both for the cortex coils 2b and 22b and for the mastoid coils 2a and 22a, can be provided with a correspondingly high number of windings and winding layers at least partially comprising different windings.

REFERENCE NUMERALS

1, 21 headband
2a, 22a mastoid coil
2b, 22b cortex coil
3 current source
4, 24 controller
5, 25 display device (display, HD retina display)
6, 26 input device (touch screen, voice recognition)
7, 27 loudspeaker
8, 28 heated area or heating pad
9a serial data interface (RS232)
9b audio interface
9c data interface (Bluetooth)
10 memory module
11 controller
12 memory (EEPROM)
13 RTC (real time)

14 reset
15 clock
16 D/A converter
17 output amplifier
18 voltage processing
19, 29 ear cup of the headphone
30 coil
31, 31' helical winding
32, 32' orthocyclic winding

The invention claimed is:

1. A device for generating alternating magnetic fields for inducing eddy currents in an organism for treating tinnitus, comprising
   a head part,
   a current source,
   a controller, and
   one or more coils,
wherein at least one coil of the one or more coils comprises at least two layers with different windings, one layer of the at least two layers with orthocyclic winding and one layer of the at least two layers with helical winding.

2. The device according to claim 1, wherein the at least two layers are adjacent layers.

3. The device according to claim 1, wherein the at least one coil is disposed in or on a headphone, and in or on an ear cup of the headphone.

4. The device according to claim 1, wherein the organism is a human with ears, the one or more coils consisting of two coils which are assigned to each ear at different height levels.

5. The device according to claim 4, wherein the coils assigned to each ear are operated in a push-pull mode.

6. The device according to claim 1, wherein the device comprises an astable multivibrator with at least one transistor, and at least one bipolar iron-core coil for emitting the alternating magnetic fields.

7. The device according to claim 1, wherein the one or more coils operate at a frequency selected between 3 and 15 Hz.

8. The device according to claim 7, wherein digital wobbling of the frequency by ±50%, is provided.

9. The device according to claim 1, wherein a 9 volt direct voltage source, is provided as the current source.

10. The device according to claim 1, wherein the device additionally comprises at least one LCD display.

11. The device according to claim 1, wherein the device additionally comprises an input device and a display device.

12. The device according to claim 1, wherein the device additionally comprises loudspeakers for sound output.

13. The device according to claim 1, wherein the device additionally comprises at least one heated area(s).

14. The device according to claim 1, wherein the device additionally comprises a data interface.

15. The device according to claim 1, wherein the device additionally comprises a memory module.

16. A method comprising:
   treating ear noises, sleep disorder, headache, migraine, cervical and thoracic syndromes, nervousness and circulatory disorder in the organism by generating an alternating negative field to induce eddy currents using the device according to claim 1.

* * * * *